United States Patent [19]

Kok et al.

[11] Patent Number: 4,656,047

[45] Date of Patent: Apr. 7, 1987

[54] RAPID METHOD FOR CELL BLOCK PREPARATION

[76] Inventors: Lanbrecht P. Kok; Mathilde E. Boon, both of Achterde Hor 2, 9304 Tn Lieveren, both of Netherlands

[21] Appl. No.: 836,939

[22] Filed: Mar. 6, 1986

[51] Int. Cl.⁴ .............................................. A01N 1/00
[52] U.S. Cl. ......................................... 427/2; 264/109; 264/239; 424/3; 427/4; 427/45.1; 427/322; 427/443
[58] Field of Search ................. 427/4, 2, 45.1, 443, 427/322; 264/109, 239; 424/3

[56] References Cited

U.S. PATENT DOCUMENTS 3,676,450  7/1972  Beightol ................................. 427/2
3,961,097  6/1976  Gravlee ................................. 424/3

FOREIGN PATENT DOCUMENTS 3047414  7/1982  Fed. Rep. of Germany .......... 424/3

OTHER PUBLICATIONS

Login GR (1978) Am. J. Med. Technol. 44:435–437.
Patterson MK et al. (1980) Stain Technol. 55:71–75.
Hopwood D. et al. (1984) Histochem. J. 16:1171–1192.
Hopwood D. et al. (1984) J. Pathol. 142:A5.
Leong ASY, et al. (1985) 146:313–321.
Login GR, et al. (1985) Am. J. Pathol. 120:230–243.

*Primary Examiner*—Norman Morgenstern
*Assistant Examiner*—Janyce A. Bell
*Attorney, Agent, or Firm*—Townsend and Townsend

[57] ABSTRACT

The preparation of paraffinized cell blocks from fixed tissue and sputum samples employs microwave enhanced dehydration and impregnation of the cell specimens. The fixed cell specimen is first exposed to a suitable dehydrating agent, typically a low molecular weight alcohol, and exposed to microwave radiation for a relatively short period of time. The dehydrated sample is then cleared (if necessary) and immersed in a suitable melted wax and thereafter exposed to microwave radiation again for a relatively short period of time. The resulting paraffinized tissue sections have been found to possess staining characteristics which are substantially equivalent or superior to those obtained by conventional cell block paraffinization techniques.

25 Claims, No Drawings

RAPID METHOD FOR CELL BLOCK PREPARATION

BACKGROUND OF THE INVENTION

1. Field of the Invention

The present invention relates generally to the fields of histology and cytology, and in particular to a rapid method for preparing paraffinized cell blocks from both tissue and sputum specimens.

The preparation of paraffinized tissue sections for examination under a light microscope typically involves fixation of a tissue specimen, preparation of a paraffinized tissue block from the fixed tissue specimen, and slicing of the block into the thin tissue sections. Preparation of the tissue block is itself a time consuming, multistep process requiring dehydration of the fixed specimen with alcohol, clearing of the alcohol with a suitable solvent, and impregnation of the specimen with a paraffin wax. Moreover, both the dehydration step and the clearing step require immersion of the specimen in a graded series of reagents for comparatively lengthy periods of time. The time required for tissue block preparation by conventional procedures is typically about 12 hours, or longer. Although the treatment times can be reduced by approximately one-third by employing vacuum-assisted immersion, the necessary treatment time is still 8 hours or longer.

Thus, it would be highly desirable to provide more rapid methods for the preparation of cell blocks from tissue specimens. It would be particularly desirable if such methods were also applicable to other cell preparation techniques, such as the preparation of cell blocks from sputum samples.

2. Description of the Relevant Art

The use of microwave energy to fix tissue specimens has been suggested. See, e.g., Login (1978) Am. J. Med. Technol. 44:435–437; Patterson and Bulard (1980) Stain Technol. 55:71–75; Hopwood et al. (1984) Histochem. J. 16:1171–1192; Hopwood et al. (1984) J. Pathol. 142:A5; Leong et al. (1985) J. Pathol. 146:313–321; and Login and Dvorak (1985) Am. J. Pathol. 120:230–243. None of these references teach the use of microwave energy in preparing paraffin cell blocks from fixed tissue specimens.

SUMMARY OF THE INVENTION

Rapid preparation of paraffinized cell blocks from fixed cell specimens is achieved by enhancing the rates of dehydration and paraffin impregnation by exposure to microwave radiation. The conventional step of clearing the dehydrating agent from the tissue sample may also be enhanced by microwave radiation, or may be eliminated by employing appropriate dehydrating agents together with microwave enhancement.

Cell specimens, which are usually tissue samples or sputum samples, are fixed by conventional methods. The fixed specimens are then immersed in a dehydrating agent, typically a low molecular weight alcohol, and exposed to microwave radiation. The intensity and duration of the microwave exposure are selected to provide substantially complete dehydration of the specimen, typically resulting in hardening of the specimen. Clearing of the dehydrating agent may also be microwave enhanced. Optionally, the need for clearing may be eliminated by employing particular dehydrating agents, such as isopropanol, which are miscible with paraffins. Use of such agents in the past was largely prevented by their slow diffusivity into the cell specimen. Microwave enhanced dehydration overcomes this problem. Finally, the cell specimen is paraffinized by immersion in a melted wax, where impregnation of the wax into the cells is enhanced by exposure to microwave radiation. The paraffinized specimen is then embedded in wax, and the resulting block is suitable for slicing into thin sections for viewing under a light microscope.

The present invention also encompasses an improved technique for microwave enhanced fixation of cell specimens. It has been found that the use of chemically reactive fixatives, such as formalin, may be greatly improved by microwave "priming" of the specimen after it has been immersed in the fixative for some time, usually at least six hours. Such priming is achieved by exposure of the specimen, while immersed in the fixative, to microwave radiation for a short period, typically about 5 minutes. Priming drives the fixation reactions within the specimen to completion, rendering the specimen completely fixed and assuring uniform analytical characteristics. This priming technique is useful not only with paraffinized tissue block preparation, but also with preparation of samples for other techniques, such as electron microscopy.

The methods of the present invention provide for a substantial reduction in the time required for preparing paraffinized cell blocks from fixed cell specimens. Where prior art methods require on the order of 12 hours for such preparation, the methods of the present invention can reduce the total preparation time to one hour or less. Moreover, such reduction in processing time is achieved without significant degradation of the quality and integrity of the resulting tissue sections. The methods have additional advantages when used for preparation cell blocks from sputum samples. The methods result in the concentration of cells on a small area of the microscope slide, as opposed to conventional smear techniques which spread the cell material thinly over the entire slide. This allows easy comparison of the architectural features and cell groupings and facilitates observing histologic differentiation of neoplastic cells. Additionally, the microwave technique results in sterilization of the sputum samples, which is a particular advantage when processing samples from patients with infectious diseases.

DESCRIPTION OF THE PREFERRED EMBODIMENT

According to the present invention, paraffinized cell blocks may be prepared from a wide variety of tissue specimens and body fluids. Suitable tissue specimens may be obtained from both humans and animals, where human tissue specimens are typically obtained by biopsy, autopsy, cell culture, and the like. Biological fluids amenable to treatment by the present invention include sputum, blood, urine, semen, and the like. In particular, methods will be described for the preparation of paraffinized cell blocks from tissue specimens and sputum samples.

Prior to cell block preparation, the cell specimens will usually be fixed by exposure to conventional fixatives, such as ethanol, buffered formaldehyde, formalin, and the like. The purpose of fixation is to convert soluble cellular substances into fixed, insoluble components with as little degradation of the biological structure as possible.

Desirably, cellular fixation may employ microwave enhancement, as described in Login, supra., Patterson et al., supra., Hopwood et al. (1984), supra., Leong et al., supra., and Login et al., supra. The disclosure of each of these references concerning microwave fixation is incorporated herein by reference. It has been found by the inventors herein, however, that the methods described in these references are not optimal, with disclosed treatment times being far too short. For fresh tissue specimens, the period of microwave exposure should be at least 30 minutes. For samples which have been previously exposed to a fixative, supplemental fixation, referred to hereinafter as priming, is desirable. Such priming involves immersion of the specimen in the same fixative followed by exposure to microwave radiation for a short period, typically 5 minutes.

When using chemically reactive fixatives, such as formalin, formaldehyde, glutaraldehydes, ruthenium red, and mixtures thereof, it is important to immerse the sample in the fixative for a minimum time period prior to exposure to microwave radiation. It has been found that microwave exposure during the initial immersion of the specimen results in fixation of the outer layers of the specimen before the fixative reaches interior portions. The fixation results in formation of a barrier which prevents further penetration of the fixative. To overcome this problem, the specimens are immersed in the fixative for a period sufficient to assure complete penetration, usually from 2 to 10 hours, more usually about 6 hours for a 1 cm thick specimen. The specimens, while still immersed, are then primed by exposure to microwave radiation for a short period, usually from 1 to 30 minutes, typically about 5 minutes, depending on the size of the sample and the power of the radiation. It will normally be desirable to maintain the temperature of the fixative below about 70° C. in order to avoid sample degradation.

In the case of sputum specimens, it is desirable to employ fixatives intended specifically for sputum. Such fixatives include those sold under the trade names Sputafix, by PAKMED, Leiden, The Netherlands. Sputum samples will typically be deposited into a microwave container containing a preselected volume of the fixative, typically from about 20 to 50 ml. The sample may then be fixed by physical and chemical processes induced by exposure to microwave radiation, leaving a hardened sample. For fresh samples, the period of exposure should be at least 30 minutes. For samples previously exposed to a fixative, priming in a microwave for a short period, typically 5 minutes, will assure complete fixation.

Once the cell specimens have been properly fixed, the method of the present invention may be employed to prepare paraffinized cell blocks where the fixed cells are impregnated and embedded in a suitable paraffin wax. The paraffinized cell blocks, in turn, are usually sliced into thin sections for viewing under a light microscope.

Preparation of the paraffinized cell blocks requires a dehydration step followed by paraffin impregnation and embedding steps. Depending on the nature of the dehydrating agent, the dehydrated cell specimens may also be cleared of the dehydrating agent prior to paraffin impregnation. Such clearing is required when the dehydrating agent is immiscible with the paraffin used for impregnation.

Dehydration of the fixed cell specimens is accomplished by exposing the specimens to a dehydrating agent, typically a low molecular weight alcohol, such as ethanol, propanol, isopropanol, butanol, isobutanol, ethyl butanol, and the like. Preferred is the use of isopropanol which is miscible with paraffins and eliminates the need for clearing. If the cells have been fixed in ethanol, no pretreatment is required prior to the dehydration step. Conversely, if the cells have been fixed in formalin or formaldehyde, it will first be necessary to bring the specimen to 70% alcohol, typically by immersing the specimen in a water bath followed by one or more alcohol baths until the desired alcohol content is achieved.

In the preferred embodiment, dehydration is accomplished by placing the specimen in ethyl propanol and thereafter exposed to microwave radiation, typically having a wavelength in the range from about 0.1 to 100 cm, more typically in the range from about 1 to 20 cm. Usually, the wavelength of about 12 cm will be employed. The temperature of the dehydration bath will be brought to a temperature in the range from about 50° to 70° C., with lower temperatures being preferred when highly labile substances are being detected. Depending on the precise temperature, the specimen will be exposed to the microwave radiation for a period in the range from about 1 to 30 minutes, usually about 2 to 15 minutes, more usually about 5 minutes. The power of the microwave energy is not critical, usually being in the range from about 200 to 1500 watts, more usually being in the range from about 300 to 1000 watts. Generally, the power will be controlled based on the temperature of the medium.

After the dehydration step is accomplished, the dehydrated specimen will be impregnated with a suitable paraffin wax, such as Paramat, available from Gurr Microscopy Materials, BDH Chemicals Ltd., Poole, England. The paraffin wax is melted, and the fixed sample placed in the melted wax in a suitable microwave container. The container is then placed in the microwave oven, and the temperature of the melted wax again raised to a final temperature in the range from about 50° to 70° C. After a sufficient time for the melted wax to permeate the sample, typically in the range from about 1 to 30 minutes, more typically in the range from about 2 to 15 minutes, usually about 5 minutes, the jar is removed from the microwave, and the sample embedded in melted paraffin wax or other embedding materials by conventional techniques.

When using dehydrating agents, which are not miscible with paraffins, the dehydrated sample must be cleared of the dehydrating agent. A suitable clearing agent, which is a solvent for the dehydrating agent and miscible in paraffin wax, is utilized. Suitable solvents include aromatic solvents, such as xylene, benzene, toluene, and the like. Various commercial preparations are available. The clearing step is utilized to complete remove the dehydrating agent, typically ethanol, from the specimen prior to impregnation with paraffin wax.

The present invention may employ commercially available microwave ovens, such as those sold for use in food preparation. Desirably, the microwave oven would provide for variable power temperature control which would allow precise temperature control of the sample being exposed to the microwave radiation. Most commercially available ovens provide on-off control where the temperature is maintained between upper and lower limits by turning off and on the microwave radiation. Although this is workable, the loss in precision and temperature control makes it more difficult to limit the temperature to below that which results in degradation of labile substances. Of course, the samples can be preserved by employing lower treatment temperatures, but this results in a lengthening of the treatment times to achieve the necessary dehydration and impregnation.

It is also preferred to use containers which are manufactured for microwave use. Such containers are essentially transparent to microwave energy and help assure that the sample is uniformly exposed to the radiation.

Once the paraffinized tissue blocks are obtained, they will be treated in a conventional manner for cytochemical or histochemical investigations. Typically, the blocks will be cut into thin slices using a microtome. The slices will usually have a thickness in the range from about 2 to 50 $\mu$m, more typically in the range from about 4 to 10 $\mu$m, usually being about 6 $\mu$m.

The sliced cellular specimens will normally be stained prior to observance under a light microscope. Numerous histochemical stains are commercially available, such as hematoxylin, eosin, reticulin, and the like. In addition to conventional stains, labelled receptors, such as antibodies, will also find use in staining substances of interest. Suitable labels include enzymes, fluorescent dyes, and the like.

The following examples are made by way of illustration, not by way of limitation.

EXPERIMENTAL

MATERIALS AND METHODS

1. Preparation of Cell Blocks from Tissue Specimens.

Biopsies were received in Leiden Fixative or in buffered 4% formalin. Leiden Fixative consists of: 0.5 alcohol 96%, 0.43 l distilled water, 0.07 l polyethylene glycol 300. The biopsy was cut into pieces 0.5 cm thick. Half of the material was subjected to the microwave method, while the other half was subjected to conventional processing without microwave stimulation.

The microwave material was placed in a glass jar containing 40 ml absolute ethanol. The biopsy which had been fixed in formalin was first placed in 40 ml 70% ethanol before being placed into the absolute ethanol. The specimen jar without a lid was then placed in a microwave oven set for 5 minutes at 50% power (FM45 Microwave Oven, 1300 $\omega$, Moulinex, Bagnolet, France). After one minute the alcohol started to boil, and, after 5 minutes almost all the alcohol was evaporated.

The hardened tissue specimen was taken out of the almost empty jar and placed in a fresh glass jar together with 40 ml Histoclear. The jar was then placed in the microwave oven at 50% power. After 5 minutes, the Histoclear reached a temperature of 70° C., below its boiling point. This tissue piece was then removed from the Histoclear and placed in a jar with 40 ml of melted Paramat (Gurr Microscopy Materials, BDH Chemicals Ltd., Poole, England). The Paramat jar was placed in the microwave oven at 50% capacity. After 5 minutes, the Paramat reached a temperature of 70° C. The Paramat jar was then removed from the microwave oven, and the tissue was embedded in melted Paramat.

The other half of each tissue specimen was conventionally processed as follows. For material fixed in Leiden Fixative the treatment consisted of 4 hours absolute alcohol, 4 hours Histoclear, and 4 hours melted Paramat. For formalin-fixed material, the biopsy was first bathed in water and then brought to 70% alcohol so that the formalin is completely removed. The remaining treatment was as for the Leiden fixed material. The processing times of both methods are summarized in Table 1 in Results.

Sections from each block were cut at 6 $\mu$m after having been cooled in the refrigerator, and were stained by a modified Papanicolaou stain (Boon and Drijver, *Routine Cytological Staining Techniques*, MacMillan, London 1986).

2. Preparation of Cell Blocks from Sputum Samples.

A Miele microwave oven, model nr M696 was used. In this oven, the desired temperature, irradiation time, and power level can be controlled. In the programming of the machine, there are two combinations possible: irradiation time and power level or maximum temperature and power level. When the maximum temperature is preset, a temperature sensor is inserted into the heat-absorbing medium. Usually this medium is a fluid in a jar made out of microwave-transparent material. When the programmed temperature is reached in the fluid, the magnetron of the microwave oven stops radiating, or radiates at shortened intervals to maintain the desired temperature. This control mechanism is rather imprecise, and the programmed temperature can be exceeded. Variations of approximately 5° C. were observed.

For fixation, fresh sputum was deposited in a microwave-transparent jar with 40 cc sputum fixing solution (Sputafix, PAKMED, Leiden, The Netherlands). This fixative is especially developed to fix sputum for cell blocking. The jar with the fixative was given to the patient, who deposited his sputum directly into the jar. The jar was then placed in the microwave oven, which was set at a power level of 450 Watt and a temperature of 60° C. After 3 minutes, the 60° C. temperature was reached, and the jar was taken out. The fixed specimen was then placed in a sachet.

For the dehydration step, the sachet with fixed sputum was placed in a jar filled with 40 ml absolute ethanol. The microwave was programmed for 70° C. and 450 Watt. The 60° C. temperature was reached after 3 minutes, and maintained for another 2 minutes. After 5 minutes, the jar was removed from the microwave. For the clearing step, the sachet with the dehydrated sputum was placed in a jar with 40 ml Pakclear, PAKMED, Leiden, The Netherlands. The microwave oven was programmed for 80° C. and 450 Watt. After 5 minutes in the microwave, the jar was removed. For the impregnating step, the sachet with the cleared sputum was placed in a jar with Paramat. The microwave oven was programmed for 80° C. and 450 Watt. After 7 minutes in the microwave, the jar was removed. The material was then embedded in warm Paramat. After cooling in the refrigerator, the resulting blocks were cut and the sections mounted. From each cell block, 4 sections were made on different levels. The sections were deparaffinized by placing them for five minutes in the microwave oven set 700 Watt. The sections were then stained with the modified Papanicolaou technique.

Smears as well as cell-block slides were prepared from two representative sputum samples. From each sample, ten microscopical fields in two smear slides and two block slides were analyzed. In each microscopical field, the number of squamous cells, metaplastic cells, alveolar macrophages, and leucocytes were counted. In addition, the nuclear size of 25 cells of each of the above mentioned cell types was established using a graphic tablet.

RESULTS

The sections of the cell blocks obtained from tissue samples by processing were excellent and virtually indistinguishable under a light microscope from the conventionally-prepared sections. Only the stroma has a slightly different appearance, in that it seemed to be somewhat more focally condensed. In contrast, the epithelium in the microwave sections is often of superior appearance. The staining characteristics achieved by the two methods were identical. In order to compare the nuclear sizes obtained by the two methods, the nuclei of various types of cells were measured. The results are given in Table 2. It is clear that there were no significant deviations in nuclear size achieved by the two methods.

TABLE 1

Times required for dehydrating, clearing, and impregnating by the microwave and by the conventional method.

| Step | Microwave | Conventional |
| --- | --- | --- |
| Dehydrating | 5 minutes | 240 minutes |
| Clearing | 5 minutes | 240 minutes |
| Impregnating | 5 minutes | 240 minutes |
| Total | 15 minutes | 720 minutes |

TABLE 2

Nuclear areas in the microwave and in the conventional method.

| Nucleus Type | Sample Size | Microwave | Conventional |
| --- | --- | --- | --- |
| Parabasal Cell Nuclei | 14 | 75 $\mu m^2$ ± 15 | 54 $\mu m^2$ ± 15 |
| Histiocytoma Nuclei | 8 | 93 $\mu m^2$ ± 30 | 81 $\mu m^2$ ± 33 |
| Stromal Cell Nuclei | 7 | 69 $\mu m^2$ ± 12 | 63 $\mu m^2$ ± 21 |
| Cylindrical Endocervix Cell Nuclei | 8 | 60 $\mu m^2$ ± 12 | 60 $\mu m^2$ ± 9 |

The changes after each step of the microwave processing in macroscopical appearance, volume, and consistency of the sputum specimens were considerable. Fresh, unfixed sputum is mucoid, whitish, sometimes having yellow or reddish tinted areas. After the fixation step, the sputum has concentrated and the consistency has become rubbery. After the dehydration step, the sputum has contracted into thread-like material and has become very hard. After the clearing step, the color of the specimen often changes into a more yellowish hue.

The cell blocks were easy to cut. The exact times, temperatures, and power levels used were established by trial and error.

In alveolar cells prepared by the microwave method, the chromatin is crisp. The cytoplasmic features and inclusions can be discerned. In different levels of the blocks, and in different parts of the sections, the cellular features were of the same superior quality.

In the sections of the cell blocks, the cellular material was condensed into small areas that could be macroscopically identified and circled. Only the circled areas on the slides were used for the cell countings. The cells in the smears were far more evenly distributed over the slides.

In Table 3, the results of the cell countings in the cell blocks and cell smears are presented. As can be seen, the number of cells per microscopic field observed with a screening magnification is much larger with sputum prepared by the microwave cell block method. Indeed, some cell types which were apparent in samples prepared by the cell block method were absent altogether from samples prepared by a conventional smear. In Table 4, the results of the nuclear measurements are given. The nuclei of cells prepared by the microwave cell block method were consistently smaller than nuclei of cells prepared by the smear. The size difference in the two methods was dependent on the cell type and was largest for nuclei of alveolar macrophages.

TABLE 3

Cell Counts for sputum for 5 patients. The numbers refer to 1 block or 1 smear per patient, for which 10 microscopic fields have been counted (magnification 40×).

| Patient | Squamous Epithelial Cells | | Metaplastic Cells | | Cylindrical Epithelial Cells | | Leukocytes | | Alveolar Macrophages | |
| --- | --- | --- | --- | --- | --- | --- | --- | --- | --- | --- |
| | Block | Smear | Block | Smear | Block | Smear | Block | Smear | Block | Smear |
| 1 | 19 | 12 | 4 | — | — | — | 206 | 64 | 395 | 337 |
| 2 | 79 | 29 | 86 | 25 | 6 | — | 606 | 324 | 107 | 22 |
| 3 | 219 | 172 | 7 | — | — | — | 667 | 133 | 74 | — |
| 4 | 78 | 7 | 5 | 2 | 7 | 3 | 385 | 68 | 18 | 42 |
| 5 | 3 | 7 | — | — | — | 1 | 220 | 42 | 381 | 202 |
| Total | 398 | 227 | 102 | 27 | 13 | 4 | 2084 | 631 | 975 | 603 |

TABLE 4

Values of nuclear area for blocked cells and smeared cells.

| Cell Type | Blocked Cells | | Smeared Cells | |
| --- | --- | --- | --- | --- |
| | Mean Value ($\mu m^2$) | Standard Deviation | Mean Value ($\mu m^2$) | Standard Deviation |
| Oral Squamous Cells | 52 | 11 | 65 | 24 |
| Metaplastic Cells | 34 | 10 | 58 | 28 |
| Alveolar Cells | 19 | 10 | 41 | 13 |
| Cylindrical Cells | 63 | 15 | 67 | 12 |

Although the foregoing invention has been described in some detail by way of illustration and example for purposes of clarity of understanding, it will be obvious that certain changes and modifications may be practiced within the scope of the appended claims.

What is claimed is:

1. A method for preparing cell blocks from fixed cell specimens, said method comprising:
   exposing the fixed cell specimen to microwave radiation in the presence of a low molecular weight alcohol whereby the specimen is dehydrated; and
   exposing the dehydrated cell specimen to microwave radiation in the presence of a melted wax whereby the specimen is impregnated with wax to form the cell block.

2. A method as in claim 1, further comprising exposing the dehydrated cell specimen to clearing reagent to remove the alcohol prior to impregnation with wax.

3. A method as in claim 2, wherein the clearing reagent is an aromatic solvent.

4. A method as in claim 3, wherein the aromatic solvent is selected from the group consisting of xylene or benzene.

5. A method as in claim 1, wherein the dehydrated cell specimen is first impregnated with melted wax followed by embedding the impregnated specimen in wax in a mold to form the cell block.

6. A method as in claim 1, wherein the cell specimen is a tissue sample.

7. A method as in claim 1, wherein the cell specimen is a sputum sample.

8. A method as in claim 1, wherein the low molecular weight alcohol is selected from the group consisting of ethanol, propanol, isopropanol, ethyl propanol, butanol, and isobutanol.

9. A method as in claim 1, wherein the wax has a melting temperature below about 70° C.

10. A method as in claim 1, wherein the specimen is subjected to microwave priming prior to dehydration after immersion in fixative for a preselected period of time.

11. A method as in claim 10, wherein the priming is achieved by exposing the specimen to microwave radiation in the presence of a fixative for a period of at least 5 minutes.

12. A method as in claim 11, wherein the fixative is a mixture of polyethylene glycol 300 and ethanol.

13. A method for preparing cell blocks from fixed cell specimens, said method comprising:

immersing the fixed cell specimen in a low molecular weight alcohol;

exposing the specimen immersed in alcohol to microwave radiation at a sufficient power level and for a sufficient time to dehydrate the specimen;

immersing the dehydrated specimen in a melted wax;

exposing the specimen immersed in wax to microwave radiation at a sufficient power level and for a sufficient time for the wax to impregnate the specimen; and embedding the impregnated specimen in an embedding material to form the cell block.

14. A method as in claim 13, wherein the low molecular weight alcohol is selected from the group consisting of ethanol, propanol, isopropanol, ethyl propanol, butanol, and isobutanol.

15. A method as in claim 13, wherein the exposure to microwave radiation while the specimen is immersed in a low molecular weight alcohol is limited so that the temperature of the alcohol does not exceed 70° C.

16. A method as in claim 15, wherein the microwave radiation has a power level in the range from 100 to 1000 W and the time of exposure is in the range from 1 to 10 minutes while the specimen is being dehydrated.

17. A method as in claim 13, wherein the exposure to microwave radiation while the specimen is immersed in wax is limited so that the temperature of the wax does not exceed 70° C.

18. A method as in claim 17, wherein the microwave radiation has a power level in the range from 100 to 1000 W and the time of exposure is in the range from 1 to 10 minutes while the specimen is being impregnated with wax.

19. An improved method for preparing a cell block from a fixed biological specimen, said method being of the type where the specimen is dehydrated with a low molecular weight alcohol, cleared with a clearing solvent, and impregnated with wax, said improvement comprising exposing the specimen to microwave radiation during at least one of the dehydrating step, the clearing step, and the impregnating step.

20. An improved method as in claim 19, wherein the specimen is exposed to microwave radiation during each of the dehydrating step, the clearing step, and the impregnating step.

21. A method for fixing cell specimens, said method comprising immersing the specimen in a chemically-reactive fixative for a time sufficient to permeate the specimen, and, thereafter exposing the specimen to microwave radiation for a time sufficient to chemically fix the specimen.

22. A method as in claim 21, wherein the specimen is a tissue sample.

23. A method as in claim 22, wherein the chemically-reactive fixative is selected from the group consisting of formalin, formaldehyde, glutaraldehyde, ruthenium red, and mixtures thereof.

24. A method as in claim 21, wherein the specimen is immersed in the fixative for from 2 to 10 hours prior to exposure to microwave radiation.

25. A method as in claim 24, wherein the microwave exposure period is from 1 to 30 minutes.

* * * * *